United States Patent
Lestrange et al.

(10) Patent No.: US 11,577,503 B2
(45) Date of Patent: Feb. 14, 2023

(54) FOUNTAIN SOLUTION THICKNESS CONTROL SYSTEM IN A DIGITAL PRINTING DEVICE USING A DRAG FORCE SENSOR

(71) Applicant: Xerox Corporation, Norwalk, CT (US)

(72) Inventors: Jack T. Lestrange, Macedon, NY (US); Joseph C. Sheflin, Macedon, NY (US); Palghat S. Ramesh, Pittsford, NY (US); Anthony S. Condello, Webster, NY (US); Brian M. Balthasar, N Tonawanda, NY (US); Seemit Praharaj, Webster, NY (US); Chu-heng Liu, Penfield, NY (US); Paul J. Mcconville, Webster, NY (US); Douglas K. Herrmann, Webster, NY (US); Jason M. Lefevre, Penfield, NY (US)

(73) Assignee: Xerox Corporation, Norwalk, CT (US)

( * ) Notice: Subject to any disclaimer, the term of this patent is extended or adjusted under 35 U.S.C. 154(b) by 206 days.

(21) Appl. No.: 17/177,262

(22) Filed: Feb. 17, 2021

(65) Prior Publication Data
US 2022/0258464 A1     Aug. 18, 2022

(51) Int. Cl.
*B41F 33/00*     (2006.01)
*B41M 1/06*     (2006.01)
*G01F 1/28*     (2006.01)
*G01N 33/32*     (2006.01)

(52) U.S. Cl.
CPC ......... *B41F 33/0063* (2013.01); *B41M 1/06* (2013.01); *G01F 1/28* (2013.01); *G01N 33/32* (2013.01)

(58) Field of Classification Search
CPC ......... B41F 33/0063; B41M 1/06; G01F 1/28; G01F 1/30; G01N 33/32
See application file for complete search history.

(56) References Cited

U.S. PATENT DOCUMENTS

| | | | |
|---|---|---|---|
| 2003/0133728 A1 * | 7/2003 | Caruthers | G03G 15/169 399/296 |
| 2007/0125182 A1 * | 6/2007 | Garshelis | G01R 33/038 |
| 2012/0103212 A1 | 5/2012 | Stowe et al. | |
| 2012/0103221 A1 | 5/2012 | Stowe et al. | |
| 2018/0281380 A1 * | 10/2018 | Lestrange | B41F 35/02 |

OTHER PUBLICATIONS

Co-Pending U.S. Appl. No. 17/137,473, filed Dec. 30, 2020.
Co-Pending U.S. Appl. No. 16/916,907, filed Jun. 30, 2020.
Do-ending U.S. Appl. No. 16/917,044, filed Jun. 30, 2020.

(Continued)

*Primary Examiner* — Jennifer Bahls
*Assistant Examiner* — Quang X Nguyen
(74) *Attorney, Agent, or Firm* — Caesar Rivise, PC (57) ABSTRACT

A drag force sensor on a fountain solution carrier roller surface measures drag force of a fountain solution layer on the fountain solution carrier roller surface in real-time during a printing operation. The measured drag force is used in a feedback loop to actively control the fountain solution layer thickness by adjusting the volumetric feed rate of fountain solution added onto the imaging member surface during a printing operation to reach a desired uniform thickness for the printing. This fountain solution monitoring system may be fully automated.

20 Claims, 5 Drawing Sheets

(56) References Cited

OTHER PUBLICATIONS

Co-Pending U.S. Appl. No. 17/137,516, filed Dec. 30, 2020.
Co-Pending U.S. Appl. No. 16/913,302, filed Jun. 26, 2020.
Co-Pending U.S. Appl. No. 17/137,711, filed Dec. 30, 2020.
Co-Pending U.S. Appl. No. 16/913,351, filed Jun. 26, 2020.
Co-Pending U.S. Appl. No. 17/137,626, filed Dec. 30, 2020.
Co-Pending U.S. Appl. No. 16/913,626, filed Jun. 26, 2020.
Co-Pending U.S. Appl. No. 17/149,161, filed Jan. 14, 2021.
Co-Pending U.S. Appl. No. 17/161,879, filed Jan. 29, 2021.

* cited by examiner

FOUNTAIN SOLUTION THICKNESS CONTROL SYSTEM IN A DIGITAL PRINTING DEVICE USING A DRAG FORCE SENSOR

FIELD OF DISCLOSURE

This invention relates generally to digital printing systems, and more particularly, to fountain solution deposition systems and methods for use in lithographic offset printing systems.

BACKGROUND

Conventional lithographic printing techniques cannot accommodate true high speed variable data printing processes in which images to be printed change from impression to impression, for example, as enabled by digital printing systems. The lithography process is often relied upon, however, because it provides very high quality printing due to the quality and color gamut of the inks used. Lithographic inks are also less expensive than other inks, toners, and many other types of printing or marking materials.

Ink-based digital printing uses a variable data lithography printing system, or digital offset printing system, or a digital advanced lithography imaging system. A "variable data lithography system" is a system that is configured for lithographic printing using lithographic inks and based on digital image data, which may be variable from one image to the next. "Variable data lithography printing," or "digital ink-based printing," or "digital offset printing," or digital advanced lithography imaging is lithographic printing of variable image data for producing images on a substrate that are changeable with each subsequent rendering of an image on the substrate in an image forming process.

For example, a digital offset printing process may include transferring ink onto a portion of an imaging member (e.g., fluorosilicone-containing imaging member, printing plate) having a surface or imaging blanket that has been selectively coated with a fountain solution (e.g., dampening fluid) layer according to variable image data. According to a lithographic technique, referred to as variable data lithography, a non-patterned reimageable surface of the imaging member is initially uniformly coated with the fountain solution layer. An imaging system then evaporates regions of the fountain solution layer in an image area by exposure to a focused radiation source (e.g., a laser light source, high power laser) to form pockets. A temporary pattern latent image in the fountain solution is thereby formed on the surface of the digital offset imaging member. The latent image corresponds to a pattern of the applied fountain solution that is left over after evaporation. Ink applied thereover is retained in the pockets where the laser has vaporized the fountain solution. Conversely, ink is rejected by the plate regions where fountain solution remains. The inked surface is then brought into contact with a substrate at a transfer nip and the ink transfers from the pockets in the fountain solution layer to the substrate. The fountain solution may then be removed, a new uniform layer of fountain solution applied to the printing plate, and the process repeated.

Digital printing is generally understood to refer to systems and methods of variable data lithography, in which images may be varied among consecutively printed images or pages. "Variable data lithography printing," or "ink-based digital printing," or "digital offset printing" are terms generally referring to printing of variable image data for producing images on a plurality of image receiving media substrates, the images being changeable with each subsequent rendering of an image on an image receiving media substrate in an image forming process. "Variable data lithographic printing" includes offset printing of ink images generally using specially-formulated lithographic inks, the images being based on digital image data that may vary from image to image, such as, for example, between cycles of an imaging member having a reimageable surface. Examples are disclosed in U.S. Patent Application Publication No. 2012/0103212 A1 (the '212 Publication) published May 3, 2012 based on U.S. patent application Ser. No. 13/095,714, and U.S. Patent Application Publication No. 2012/0103221 A1 (the '221 Publication) also published May 3, 2012 based on U.S. patent application Ser. No. 13/095,778.

The inventors have found that digital printing processes are sensitive to the amount of fountain solution applied to the imaging member blanket. If too much fountain solution is applied to the imaging member surface, then the laser may not be able to boil/evaporate the fountain solution and no image will be created on the blanket. If too little fountain solution is applied to the imaging member surface, then the ink will not be rejected in the non-imaged regions leading to high background. Currently, there is no way to measure how much fountain solution is deposited on the imaging member blanket in real-time during a printing operation. Further, current fountain solution systems operate open loop, where the amount of fountain solution is manually adjustable based on image quality of previous print jobs. In this state, fountain solution systems are at the mercy of printing device noises and may require constant manual adjustments.

SUMMARY

The following presents a simplified summary in order to provide a basic understanding of some aspects of one or more embodiments or examples of the present teachings. This summary is not an extensive overview, nor is it intended to identify key or critical elements of the present teachings, nor to delineate the scope of the disclosure. Rather, its primary purpose is merely to present one or more concepts in simplified form as a prelude to the detailed description presented later. Additional goals and advantages will become more evident in the description of the figures, the detailed description of the disclosure, and the claims.

The foregoing and/or other aspects and utilities embodied in the present disclosure may be achieved by providing a method of controlling fountain solution thickness on an imaging member surface of a rotating imaging member in a digital image forming device. The method includes: (a) transferring a layer of fountain solution from a fountain solution applicator having a fountain solution dispense rate onto a fountain solution carrier roller, (b) measuring a drag force of the fountain solution layer between a sensor head and the fountain solution carrier roller, with the fountain solution layer being a lubricant between the sensor head and the fountain solution carrier roller, (c) modifying the fountain solution dispense rate based on the measured drag force, and (d) applying a subsequent fountain solution layer at the modified fountain solution dispense rate onto the imaging member surface for an image forming operation thereon.

According to aspects illustrated herein, an exemplary method of controlling fountain solution thickness on an imaging member surface of a rotating imaging member in a digital image forming device, with the digital image forming device printing a current image onto a print substrate. The printing includes applying a fountain solution layer at a dispense rate onto the imaging member surface with the fountain solution fluid layer having a surface above the imaging member surface, vaporizing in an image wise fashion a portion of the fountain solution layer to form a latent image, applying ink onto the latent image over the imaging member surface, and transferring the applied ink from the imaging member surface to the print substrate. The method of controlling fountain solution thickness includes transferring the layer of fountain solution from a fountain solution applicator having a fountain solution dispense rate onto a fountain solution carrier roller, measuring a drag force of the fountain solution layer between a sensor head and the fountain solution carrier roller, with the fountain solution layer being a lubricant between the sensor head and the fountain solution carrier roller, modifying the fountain solution dispense rate based on the measured drag force, and printing a subsequent image by the digital image forming device using the modified fountain solution dispense rate.

In examples, after measuring drag force of the fountain solution fluid layer surface, the methods may include comparing the measured drag force value to a target drag force value and/or estimating a thickness of the applied fountain solution fluid layer based on the measured drag force value and then comparing the estimated thickness of the applied fountain solution fluid layer with a target thickness. In such examples the step of modifying the fountain solution dispense rate based on the measured drag force value may include modifying the fountain solution dispense rate based on the comparison between the measured drag force value and the target drag force value, modifying the fountain solution dispense rate based on the estimated thickness of the applied fountain solution fluid layer, and/or modifying the fountain solution dispense rate based on the comparison between the estimated thickness of the applied fountain solution fluid layer and the target thickness.

According to aspects described herein, an exemplary digital image forming device controls fountain solution thickness on an imaging member surface of a rotating imaging member. The digital image forming device may include a fountain solution carrier roller, a fountain solution applicator, a drag force sensor, and a controller. The fountain solution applicator may be configured to apply a fountain solution fluid layer at a dispense rate, with the fountain solution fluid layer being transferred onto the fountain solution carrier roller. The drag force sensor may include a sensor head adjacent the fountain solution carrier roller and in contact with the fountain solution fluid layer, with the sensor configured to measure a drag force of the fountain solution layer between the sensor head and the fountain solution carrier roller, and the fountain solution layer being a lubricant between the sensor head and the fountain solution carrier roller. The controller is in communication with the sensor and the fountain solution applicator to modify the fountain solution dispense rate based on the measured drag force. The fountain solution applicator is further configured to apply a subsequent fountain solution layer at the modified fountain solution dispense rate onto the imaging member surface for an image forming operation thereon.

Exemplary embodiments are described herein. It is envisioned, however, that any system that incorporates features of apparatus and systems described herein are encompassed by the scope and spirit of the exemplary embodiments.

BRIEF DESCRIPTION OF THE DRAWINGS

Various exemplary embodiments of the disclosed apparatuses, mechanisms and methods will be described, in detail, with reference to the following drawings, in which like referenced numerals designate similar or identical elements, and.

DETAILED DESCRIPTION

Illustrative examples of the devices, systems, and methods disclosed herein are provided below. An embodiment of the devices, systems, and methods may include any one or more, and any combination of, the examples described below. This invention may, however, be embodied in many different forms and should not be construed as limited to the embodiments set forth below. Rather, these exemplary embodiments are provided so that this disclosure will be thorough and complete, and will fully convey the scope of the invention to those skilled in the art. Accordingly, the exemplary embodiments are intended to cover all alternatives, modifications, and equivalents as may be included within the spirit and scope of the apparatuses, mechanisms and methods as described herein.

We initially point out that description of well-known starting materials, processing techniques, components, equipment and other well-known details may merely be summarized or are omitted so as not to unnecessarily obscure the details of the present disclosure. Thus, where details are otherwise well known, we leave it to the application of the present disclosure to suggest or dictate choices relating to those details. The drawings depict various examples related to embodiments of illustrative methods, apparatus, and systems for inking from an inking member to the reimageable surface of a digital imaging member.

When referring to any numerical range of values herein, such ranges are understood to include each and every number and/or fraction between the stated range minimum and maximum. For example, a range of 0.5-6% would expressly include the endpoints 0.5% and 6%, plus all intermediate values of 0.6%, 0.7%, and 0.9%, all the way up to and including 5.95%, 5.97%, and 5.99%. The same applies to each other numerical property and/or elemental range set forth herein, unless the context clearly dictates otherwise.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value. For example, the term "about 2" also discloses the value "2" and the range "from about 2 to about 4" also discloses the range "from 2 to 4."

The term "controller" or "control system" is used herein generally to describe various apparatus such as a computing device relating to the operation of one or more device that directs or regulates a process or machine. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

Embodiments as disclosed herein may also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, and the like that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described therein.

Although embodiments of the invention are not limited in this regard, discussions utilizing terms such as, for example, "processing," "computing," "calculating," "determining," "using," "establishing", "analyzing", "checking", or the like, may refer to operation(s) and/or process(es) of a controller, computer, computing platform, computing system, or other electronic computing device, that manipulate and/or transform data represented as physical (e.g., electronic) quantities within the computer's registers and/or memories into other data similarly represented as physical quantities within the computer's registers and/or memories or other information storage medium that may store instructions to perform operations and/or processes.

The terms "media", "print media", "print substrate" and "print sheet" generally refers to a usually flexible physical sheet of paper, polymer, Mylar material, plastic, or other suitable physical print media substrate, sheets, webs, etc., for images, whether precut or web fed. The listed terms "media", "print media", "print substrate" and "print sheet" may also include woven fabrics, non-woven fabrics, metal films, and foils, as readily understood by a skilled artisan.

The term "image forming device", "printing device" or "printing system" as used herein may refer to a digital copier or printer, scanner, image printing machine, xerographic device, electrostatographic device, digital production press, document processing system, image reproduction machine, bookmaking machine, facsimile machine, multi-function machine, or generally an apparatus useful in performing a print process or the like and can include several marking engines, feed mechanism, scanning assembly as well as other print media processing units, such as paper feeders, finishers, and the like. A "printing system" may handle sheets, webs, substrates, and the like. A printing system can place marks on any surface, and the like, and is any machine that reads marks on input sheets; or any combination of such machines.

The term "fountain solution" or "dampening fluid" refers to dampening fluid that may coat or cover a surface of a structure (e.g., imaging member, transfer roll) of an image forming device to affect connection of a marking material (e.g., ink, toner, pigmented or dyed particles or fluid) to the surface. The fountain solution may include water optionally with small amounts of additives (e.g., isopropyl alcohol, ethanol) added to reduce surface tension as well as to lower evaporation energy necessary to support subsequent laser patterning. Low surface energy solvents, for example volatile silicone oils, can also serve as fountain solutions. Fountain solutions may also include wetting surfactants, such as silicone glycol copolymers. The fountain solution may include D4 or D5 dampening fluid alone, mixed, and/or with wetting agents. The fountain solution may also include Isopar G, Isopar H, Dowsil OS10, Dowsil OS20, Dowsil OS30, and mixtures thereof.

Inking systems or devices may be incorporated into digital offset image forming device architecture so that the inking system is arranged about a central imaging plate, also referred to as an imaging member. In such a system, the imaging member is a rotatable imaging member, including a conformable blanket around a cylindrical drum with the conformable blanket including the reimageable surface. This blanket layer has specific properties such as composition, surface profile, and so on so as to be well suited for receipt and carrying a layer of a fountain solution. A surface of the imaging member is reimageable making the imaging member a digital imaging member. The surface is constructed of elastomeric materials and conformable. A paper path architecture may be situated adjacent the imaging member to form a media transfer nip.

A layer of fountain solution may be applied to the surface of the imaging member by a dampening system. In a digital evaporation step, particular portions of the fountain solution layer deposited onto the surface of the imaging member may be evaporated by a digital evaporation system. For example, portions of the fountain solution layer may be vaporized by an optical patterning subsystem such as a scanned, modulated laser that patterns the fluid solution layer to form a latent image. In a vapor removal step, the vaporized fountain solution may be collected by a vapor removal device or vacuum to prevent condensation of the vaporized fountain solution back onto the imaging plate.

In an inking step, ink may be transferred from an inking system to the surface of the imaging member such that the ink selectively resides in evaporated voids formed by the patterning subsystem in the fountain solution layer to form an inked image. In an image transfer step, the inked image is then transferred to a print substrate such as paper via pressure at the media transfer nip.

In a digital variable printing process, previously imaged ink must be removed from the imaging member surface to prevent ghosting. After an image transfer step, the surface of the imaging member may be cleaned by a cleaning system so that the printing process may be repeated. For example, tacky cleaning rollers may be used to remove residual ink and fountain solution from the surface of the imaging member.

A drawback of digital print processes is print quality sensitivity to the amount of fountain solution deposited onto the imaging blanket. It is estimated that a very thin layer of fountain solution (e.g., 30-100 nm thickness range) is required on the blanket for optimal print process setup. This makes measuring the fountain solution thickness on the imaging blanket most difficult.

Figure 1:
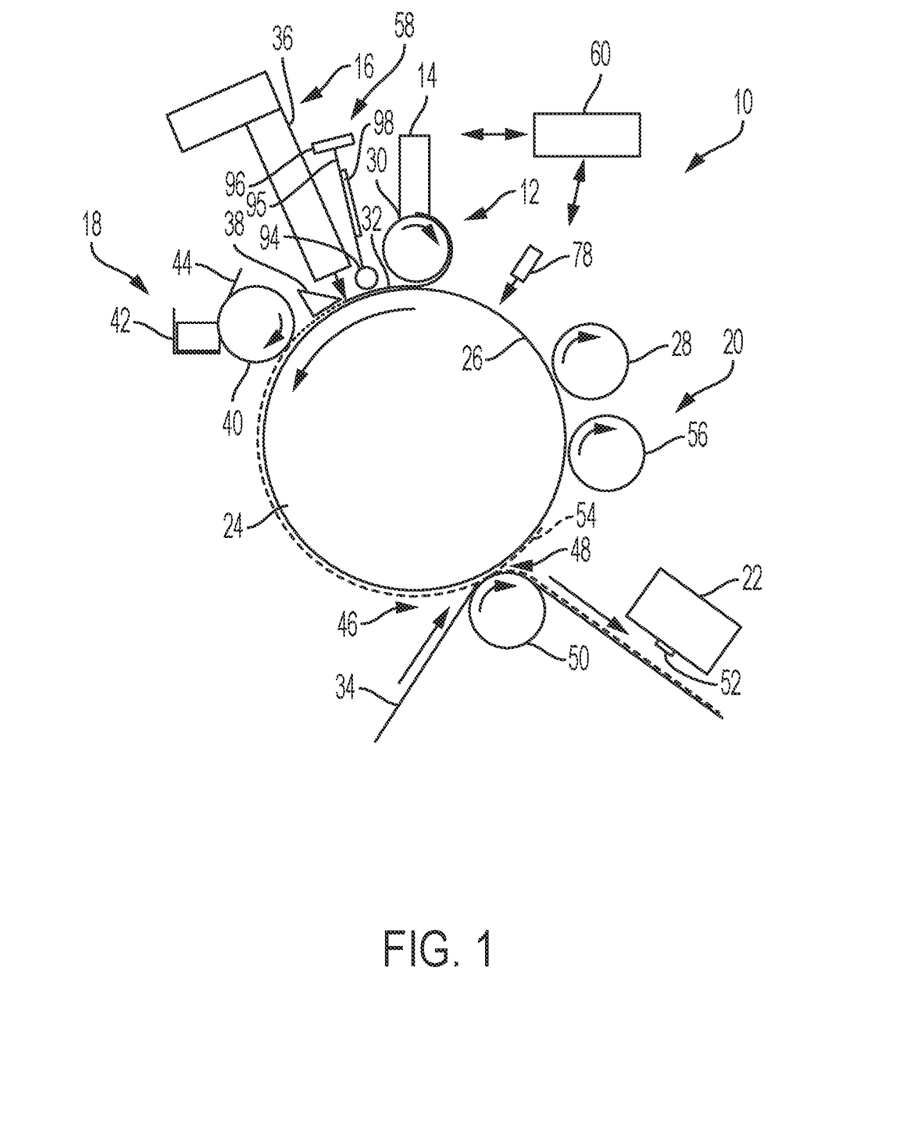
FIG. 1 is block diagram of a digital image forming device in accordance with examples of the embodiments.

FIG. 1 depicts an exemplary ink-based digital image forming device 10. The image forming device 10 may include dampening station 12 having fountain solution applicator 14, optical patterning subsystem 16, inking apparatus 18, and a cleaning device 20. The image forming device 10 may also include one or more rheological conditioning subsystems 22 as discussed, for example, in greater detail below. FIG. 1 shows the fountain solution applicator 14 arranged with a digital imaging member 24 having a reimageable surface 26. While FIG. 1 shows components that are formed as rollers, other suitable forms and shapes may be implemented.

The imaging member surface 26 may be wear resistant and flexible. The surface 26 may be reimageable and conformable, having an elasticity and durometer, and sufficient flexibility for coating ink over a variety of different media types having different levels of roughness. A thickness of the reimageable surface layer may be, for example, about 0.5 millimeters to about 4 millimeters. The surface 26 should have a weak adhesion force to ink, yet good oleophilic wetting properties with the ink for promoting uniform inking of the reimageable surface and subsequent transfer lift of the ink onto a print substrate.

The soft, conformable surface 26 of the imaging member 24 may include, for example, hydrophobic polymers such as silicones, partially or fully fluorinated fluorosilicones and FKM fluoroelastomers. Other materials may be employed, including blends of polyurethanes, fluorocarbons, polymer catalysts, platinum catalyst, hydrosilyation catalyst, etc. The surface may be configured to conform to a print substrate on which an ink image is printed. To provide effective wetting of fountain solutions such as water-based dampening fluid, the silicone surface need not be hydrophilic, but may be hydrophobic. Wetting surfactants, such as silicone glycol copolymers, may be added to the fountain solution to allow the fountain solution to wet the reimageable surface 26. The imaging member 24 may include conformable reimageable surface 26 of a blanket or belt wrapped around a roll or drum. The imaging member surface 26 may be temperature controlled to aid in a printing operation. For example, the imaging member 24 may be cooled internally (e.g., with chilled fluid) or externally (e.g., via a blanket chiller roll to a temperature (e.g., about 10° C.-60° C.) that may aid in the image forming, transfer and cleaning operations of image forming device 10.

The reimageable surface 26 or any of the underlying layers of the reimageable belt/blanket may incorporate a radiation sensitive filler material that can absorb laser energy or other highly directed energy in an efficient manner. Examples of suitable radiation sensitive materials are, for example, microscopic (e.g., average particle size less than 10 micrometers) to nanometer sized (e.g., average particle size less than 1000 nanometers) carbon black particles, carbon black in the form of nano-particles of, single or multi-wall nanotubes, graphene, iron oxide nano-particles, nickel plated nano-particles, etc., added to the polymer in at least the near-surface region. It is also possible that no filler material is needed if the wavelength of a laser is chosen so to match an absorption peak of the molecules contained within the fountain solution or the molecular chemistry of the outer surface layer. As an example, a 2.94 μm wavelength laser would be readily absorbed due to the intrinsic absorption peak of water molecules at this wavelength.

The fountain solution applicator 14 may be configured to deposit a layer of fountain solution onto the imaging member surface 26 directly or via an intermediate member (e.g., roller 30) of the dampening station 12. While not being limited to particular configuration, the fountain solution applicator 14 may include a series of rollers, sprays or a vaporizer (not shown) for uniformly wetting the reimageable surface 26 with a uniform layer of fountain solution with the thickness of the layer being controlled. The series of rollers may be considered as dampening rollers or a dampening unit, for uniformly wetting the reimageable surface 26 with a layer of fountain solution. The fountain solution may be applied by fluid or vapor deposition to create a thin fluid layer 32 (e.g., between about 0.01 μm and about 1.0 μm in thickness, less than 5 μm, about 50 nm to 100 nm) of the fountain solution for uniform wetting and pinning. The applicator 14 may include a slot at its output across the imaging member 26 or intermediate roller 30 to output fountain solution to the imaging member surface 26.

Figure 2:
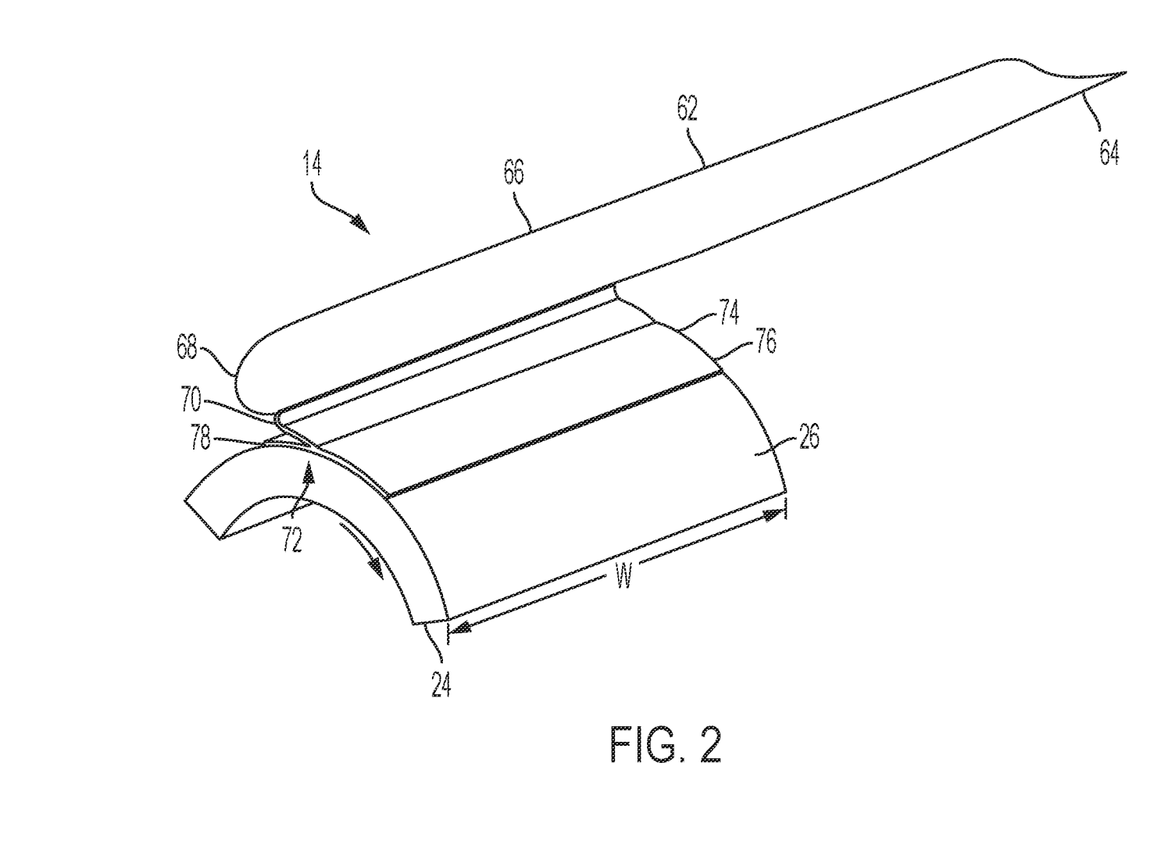
FIG. 2 is a perspective view of an exemplary fountain solution applicator.

FIG. 2 depicts another exemplary fountain solution applicator 14 that may apply a fountain solution layer directly onto the imaging member surface 26. The fountain solution applicator 14 includes a supply chamber 62 that may be generally cylindrical defining an interior for containing fountain solution vapor therein. The supply chamber 62 includes an inlet tube 64 in fluid communication with a fountain solution supply (not shown), and a tube portion 66 extending to a closed distal end 68 thereof. A supply channel 70 extends from the supply chamber 62 to adjacent the imaging member surface 26, with the supply channel defining an interior in communication with the interior of the supply chamber to enable flow of fountain solution vapor from the supply chamber through the supply channel and out a supply channel outlet slot 72 for deposition over the imaging member surface, where the fountain solution vapor condenses to a fluid on the imaging member surface.

A vapor flow restriction boarder 74 extends from the supply channel 70 adjacent the reimageable surface 26 to confine fountain solution vapor provided from the supply channel outlet slot 72 to a condensation region defined by the restriction boarder and the adjacent reimageable surface to support forming a layer of fountain solution on the reimageable surface via condensation of the fountain solution vapor onto the reimageable surface. The restriction boarder 74 defines the condensation region over the surface 26 of the imaging member 24. The restriction boarder includes arc walls 76 that face the imaging member surface 26, and boarder wall 78 that extends from the arc walls towards the imaging member surface. The reimageable surface 26 of the imaging member 24 may have a width W parallel to the supply channel 70 and supply channel outlet slot 72, with the outlet slot having a width across the imaging member configured to enable fountain solution vapor in the supply chamber interior to communicate with the imaging member surface across its width. In examples where the fountain solution applicator 14 deposits fountain solution vapor onto the imaging member surface 26 that condenses to form the fountain solution layer 32, excess vapor may be collected and removed after sufficient condensation, for example, via a vacuum or other vapor removal device (not shown) to prevent condensation of the vaporized fountain solution back onto the imaging plate.

Referring back to FIG. 1 the optical patterning subsystem 16 is located downstream the fountain solution applicator 14 and the drag force meter 58 in the printing processing direction to selectively pattern a latent image in the layer of fountain solution by image-wise patterning using, for example, laser energy. In examples, the fountain solution layer is exposed to an energy source (e.g. a laser) that selectively applies energy to portions of the layer to image-wise evaporate the fountain solution and create a latent "negative" of the ink image that is desired to be printed on a receiving substrate 34. Image areas are created where ink is desired, and non-image areas are created where the fountain solution remains. While the optical patterning subsystem 16 is shown as including laser emitter 36, it should be understood that a variety of different systems may be used to deliver the optical energy to pattern the fountain solution layer.

A vapor vacuum 38 or air knife may be positioned downstream the optical patterning subsystem to collect vaporized fountain solution and thus avoid leakage of excess fountain solution into the environment. Reclaiming excess vapor prevents fountain solution from depositing uncontrollably prior to the inking apparatus 18 and imaging member 24 interface. The vapor vacuum 38 may also prevent fountain solution vapor from entering the environment. Reclaimed fountain solution vapor can be condensed, filtered and reused as understood by a skilled artisan to help minimize the overall use of fountain solution by the image forming device 10.

Following patterning of the fountain solution layer by the optical patterning subsystem 16, the patterned layer over the reimageable surface 26 is presented to the inking apparatus 18. The inker apparatus 18 is positioned downstream the optical patterning subsystem 16 to apply a uniform layer of ink over the layer of fountain solution and the reimageable surface layer 26 of the imaging member 24. The inking apparatus 18 may deposit the ink to the evaporated pattern representing the imaged portions of the reimageable surface 26, while ink deposited on the unformatted portions of the fountain solution will not adhere based on a hydrophobic and/or oleophobic nature of those portions. The inking apparatus may heat the ink before it is applied to the surface 26 to lower the viscosity of the ink for better spreading into imaged portion pockets of the reimageable surface. For example, one or more rollers 40 of the inking apparatus 18 may be heated, as well understood by a skilled artisan. Inking roller 40 is understood to have a structure for depositing marking material onto the reimageable surface layer 26, and may include an anilox roller or an ink nozzle. Excess ink may be metered from the inking roller 40 back to an ink container 42 of the inker apparatus 18 via a metering member 44 (e.g., doctor blade, air knife).

Although the marking material may be an ink, such as a UV-curable ink, the disclosed embodiments are not intended to be limited to such a construct. The ink may be a UV-curable ink or another ink that hardens when exposed to UV radiation. The ink may be another ink having a cohesive bond that increases, for example, by increasing its viscosity. For example, the ink may be a solvent ink or aqueous ink that thickens when cooled and thins when heated.

Downstream the inking apparatus 18 in the printing process direction resides ink image transfer station 46 that transfers the ink image from the imaging member surface 26 to a print substrate 34. The transfer occurs as the substrate 34 is passed through a transfer nip 48 between the imaging member 24 and an impression roller 50 such that the ink within the imaged portion pockets of the reimageable surface 26 is brought into physical contact with the substrate 34 and transfers via pressure at the transfer nip from the imaging member surface to the substrate as a print of the image.

Rheological conditioning subsystems 22 may be used to increase the viscosity of the ink at specific locations of the digital offset image forming device 10 as desired. While not being limited to a particular theory, rheological conditioning subsystem 22 may include a curing mechanism 52, such as a UV curing lamp (e.g., standard laser, UV laser, high powered UV LED light source), wavelength tunable photoinitiator, or other UV source, that exposes the ink to an amount of UV light (e.g., #of photons radiation) to at least partially cure the ink/coating to a tacky or solid state. The curing mechanism may include various forms of optical or photo curing, thermal curing, electron beam curing, drying, or chemical curing. In the exemplary image forming device 10 depicted in FIG. 1, rheological conditioning subsystem 22 may be positioned adjacent the substrate 34 downstream the ink image transfer station 46 to cure the ink image transferred to the substrate. Rheological conditioning subsystems 22 may also be positioned adjacent the imaging member surface 26 between the ink image transfer station 46 and cleaning device 20 as a preconditioner to harden any residual ink 54 for easier removal from the imaging member surface 26 that prepares the surface to repeat the digital image forming operation.

This residual ink removal is most preferably undertaken without scraping or wearing the imageable surface of the imaging member. Removal of such remaining fluid residue may be accomplished through use of some form of cleaning device 20 adjacent the surface 26 between the ink image transfer station 46 and the fountain solution applicator 14. Such a cleaning device 20 may include at least a first cleaning member 56 such as a sticky or tacky roller in physical contact with the imaging member surface 26, with the sticky or tacky roller removing residual fluid materials (e.g., ink, fountain solution) from the surface. The sticky or tacky roller may then be brought into contact with a smooth roller (not shown) to which the residual fluids may be transferred from the sticky or tacky member, the fluids being subsequently stripped from the smooth roller by, for example, a doctor blade or other like device and collected as waste. It is understood that the cleaning device 20 is one of numerous types of cleaning devices and that other cleaning devices designed to remove residual ink/fountain solution from the surface of imaging member 24 are considered within the scope of the embodiments. For example, the cleaning device could include at least one roller, brush, web, belt, tacky roller, buffing wheel, etc., as well understood by a skilled artisan.

Figure 6:
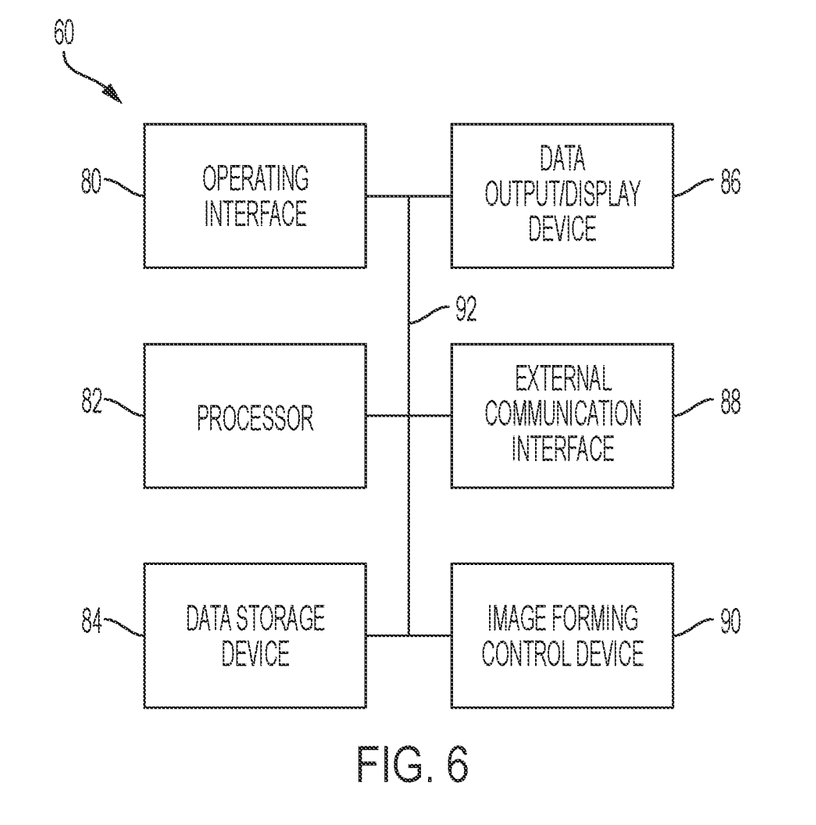
FIG. 6 is a block diagram of a controller for executing instructions to control the digital image forming device.

In the image forming device 10, functions and utility provided by the dampening station 12, optical patterning subsystem 16, inking apparatus 18, cleaning device 20, rheological conditioning subsystems 22, imaging member 24 and drag force meter 58 may be controlled, at least in part by controller 60. Such a controller 60 is shown in FIGS. 1 and 6, and may be further designed to receive information and instructions from a workstation or other image input devices (e.g., computers, smart phones, laptops, tablets, kiosk) to coordinate the image formation on the print substrate through the various subsystems such as the dampening station 12, patterning subsystem 16, inking apparatus 18, imaging member 24 and drag force meter 58 as discussed in greater detail herein and understood by a skilled artisan.

As noted above, currently there is no way to measure how much fountain solution is deposited on the imaging member blanket surface 26 in real-time automatically or during a printing operation. One drawback in trying to measure the thickness of fountain solution directly on the imaging blanket is that the top surface of the blanket is coated with a fluorosilicone/carbon black solution. The carbon black is added to absorb the laser light during the imaging process. The carbon black also makes it very difficult to measure the fountain solution on the blanket during image forming operations using a non-contact specular sensor because light is absorbed by the blanket. Such specular sensors researched as potential solutions have been very expensive and impractical, especially since one specular sensor system would have to be purchased several (e.g., 3-5) times for use in color printers. An additional drawback of the fluorosilicone/carbon black imaging member surface is that any contact sensors scuff/abrade the surface causing defects objectionable in the print.

Figure 3:
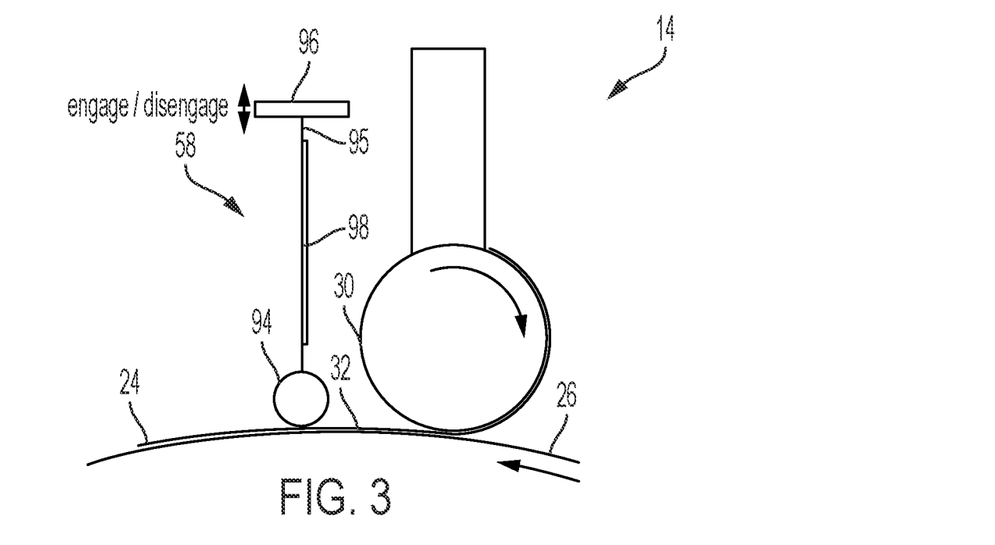
FIG. 3 is an enlarged view of an exemplary drag force sensor in position to measure fountain solution drag force on an imaging member.
Figure 4:
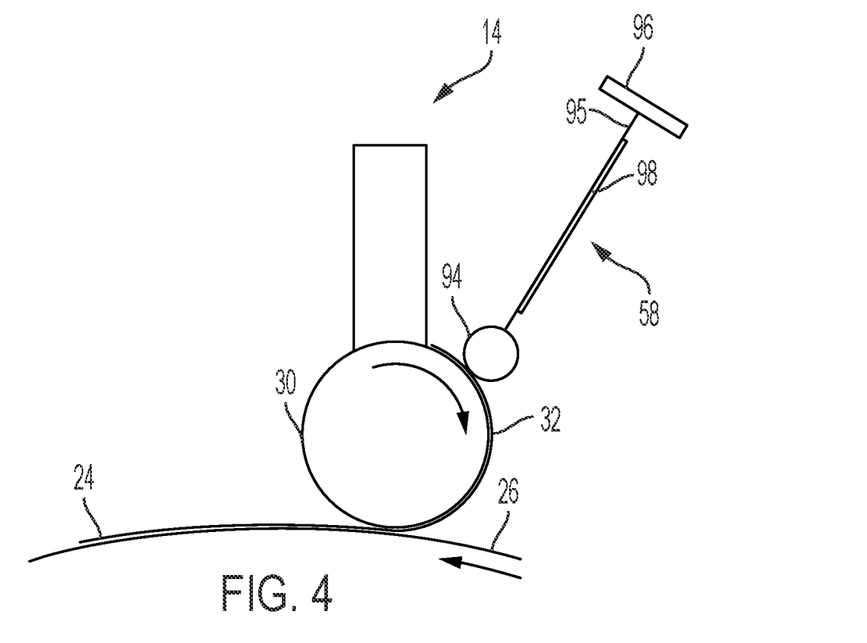
FIG. 4 is an enlarged view of an exemplary drag force sensor in position to measure fountain solution drag force on an intermediate roller.

The inventors found a low cost approach to determining fountain solution thickness on the imaging member surface indirectly by measuring drag force of a deposited fountain solution layer between a drag force sensor 58 (FIGS. 1, 3 and 4) and a fountain solution carrier roller carrying the deposited fountain solution. While not being limited to a particular theory, the fountain solution carrier roller may be the imaging member 24, or another roller such as the intermediate roller 30, as discussed in greater detail below. In FIGS. 1 and 3, the fountain solution carrier roller is shown as the imaging member 24. In FIG. 4, the fountain solution carrier roller is shown as intermediate roller 30, which may be part of or downstream the fountain solution applicator 14 before the imaging member. Generally the fountain solute carrier roller may be any roller (e.g., cylindrical, spherical ellipsoidal, spheroidal) configured to receive a layer or film of fountain solution directly or indirectly from the fountain solution applicator 14 at a dispense rate. The dispense rate may be set and modified by input from the controller 60 to arrive at a desired corresponding fountain solution layer thickness 32 on the imaging member 24.

FIG. 3 depicts an example of the drag force sensor 58 in position to measure drag force between the sensor head and the fountain solution carrier roller, which in this example is the imaging member 24. In examples the drag force sensor 58 may include a sensor head 94 in contact with the imaging member surface 26 and/or a fountain solution layer on the imaging member surface for measurement. The sensor head 94 may attach to a sensor housing 96 directly or indirectly (e.g., via a coupling rod 95 having a strain gauge 98). The drag force sensor 58 may also shift into and out of engagement with the fountain solution carrier roller as desired. For example, the sensor 58 may include a displacement unit (not shown) including, for example, a servo motor for moving the sensor head 94 into engagement with the fountain solution carrier roller to measure drag or drag force change caused by fountain solution on the carrier roller. The displacement unit may move the sensor head 94 away from the fountain solution carrier roller when no measurement is needed to help minimize wear on the sensor head or the carrier roller.

The sensor head 94 shown in FIG. 3 may be in contact with the imaging member surface 26 or blanket at any position across the width of the imaging member 24. The sensor head 94 is not limited by shape, and may be spherical, cylindrical, ellipsoidal or other shapes sensitive to fountain solution drag forces on the carrier roller, as well understood by a skilled artisan. For example, the sensor head 94 may have a carrier roller conforming curved surface for use proximate or against the carrier roller surface with additional surface area to increase signal to noise ratios of the sensor. It is also understood that the imaging member surface has a width greater than the general active printing zone or imageable region where imaging occurs. In examples the sensor head 94 may contact the imaging member surface outside the active printing zone to avoid disturbing the fountain solution layer 32 in the imageable region of the imaging member surface, and thus not affect actual printings of the image forming device 10.

FIG. 4 depicts an example of the drag force sensor 58 in position to measure drag force between the sensor head and the fountain solution carrier roller, which in this example is the intermediate roller 30. The drag force sensors 58 shown in FIGS. 3 and 4 are like elements, with the drag force sensor in FIG. 4 also including the sensor head 94, sensor housing 96, coupling rod 95 having a strain gauge 98, and displacement unit substantially as discussed by example above. In examples as shown in FIG. 4, the fountain solution applicator 14 deposits fountain solution onto the intermediate roller 30 at a dispense rate. The deposited fountain solution forms a fountain solution film or layer on the intermediate roller, which transfers the fountain solution film onto the imaging member surface 26 indirectly or directly, such as at a nip therebetween. In examples where the intermediate roller 30 directly contacts the conformable imaging member surface 26, the intermediate roller may have a hard surface (e.g., aluminum, stainless steel). In such examples, the sensor head 94 may also have a conformable surface that interacts with the hard surface of the intermediate roller.

The sensor head 94 in FIG. 4 is in contact with the intermediate roller 30 and/or a fountain solution layer on the intermediate roller surface for measurement of drag force caused by the fountain solution layer. The sensor head 94 may be in contact with the intermediate roller surface at any position across the width of the intermediate roller 30. Like the imaging member width, it's understood that the intermediate roller 30 has a width greater than the general active printing zone or imageable region of the imaging member where imaging occurs. While the sensor head may contact the intermediate roller surface an any location where fountain solution may be deposited on the intermediate roller, in examples the sensor head 94 may contact the imaging member surface where fountain solution is deposited and outside any region of the surface that corresponds to an active printing zone on the imaging member where the fountain solution would transfer onto the imaging member surface for imaging. The measured fountain solution, which may be disturbed and moved by the sensor head 94, may also transfer to the imaging member surface, but does not affect actual printings of the image forming device 10 as any disturbed measured fountain solution would be transferred outside the active printing zone of the imaging member.

Figure 5:
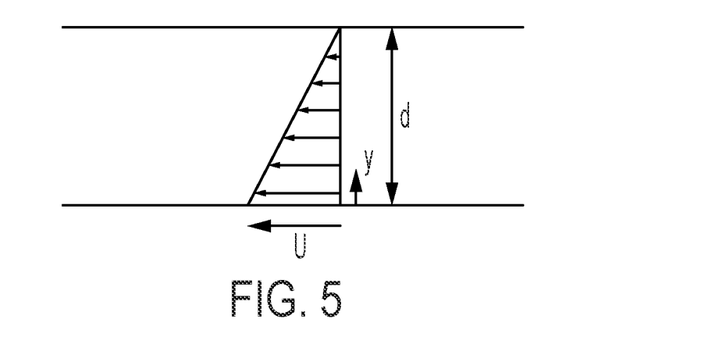
FIG. 5 is a diagram showing shear flow between parallel plates according to Newton's Law of viscosity.

The layer of fountain solution measured by the drag force sensor 58 is a dampening fluid film that may act as a lubricant between the sensor head 94 and the fountain solution carrier roller. In examples, during rotation of the fountain solution carrier roller, the sensor head 94 in contact with the carrier roller may measure drag force caused by the carrier roller rotating against the sensor head. Fountain solution on the carrier roller affects the amount of drag on the sensor head, and the drag force imparted onto the sensor head is a shear force. Shear force transmitted to the sensor head is inversely proportional to the thickness of the fountain solution layer according to Newton's Law of viscosity for parallel plate relative motion (FIG. 5).

$$\tau = \mu \frac{\partial u}{\partial y} = \mu \frac{U}{d}$$

Where:
- τ is the shear stress at any point in the fluid,
- μ is the dynamic viscosity of the fluid,
- u is the flow velocity along the boundary (e.g., surface of the carrier roller),
- y is the distance from the boundary, and
- d is the total separation gap of the parallel plates and corresponds to the thickness of the fountain solution layer The determined drag force may be used to determine thickness of the deposited fountain solution, for example according to a drag force vs fountain solution fluid thickness relationship as will be discussed in greater detail below. Such relationship may be predetermined by actual measurement offline of fountain solution thickness with, for example, a spectral reflectivity measurement device that can directly measure fountain solution thickness coinciding with a drag force measurement of the fountain solution, and storing the results, for example in in a lookup table for subsequent reference by the controller 60. When y=d at the interface with the sensor head 94, Fdrag/Area=mu*U/d at the sensor surface where Fdrag is the drag force on the sensor and Area is the contact area between the fountain solution and the sensor head.

Upon determination of the drag force on the sensor 58, the controller 60 can determine if the fountain solution deposition rate needs to be modified. It is understood that the approaches discussed herein by example to modify fountain solution thickness do not require a determination of the actual fountain solution layer thickness. Drag force to actual fountain solution thickness may be correlated such that a desired fountain solution thickness (e.g., between about 0.01 μm and about 1.0 μm, less than 5 μm, about 30-100 nm) has a corresponding drag force that the controller 60 may compare to a measured drag force and determine if the fountain solution applicator needs to increase, decrease or maintain the fountain solution dispense rate, for example with drag force inversely proportional to fountain solution thickness. Again, in examples drag force may be measured via strain on the strain gauge 98 sensor arm coupling rod 95 as drag force caused by the fountain solution layer 32 bends the coupling rod. Scope is not limited by the approach of measuring the drag/shear force on the sensor head 94, as there may be several ways (e.g., strain gauge, linear variable displacement transformer (LVDT) sensors, spring(s) with strain gauge 98, spring(s) with displacement sensor(s), torque transducer(s)) as readily understood by a skilled artisan. The drag force measurement results may thus be used over time to monitor fountain solution layer 32 thickness, and if desired, may allow the image forming device 10 to control fountain solution layer thickness by modifying the fountain solution dispense rate onto the imaging member 24 as needed to arrive at or maintain the desired fountain solution thickness. Fountain solution layer 32 thickness quality control monitoring may be applied automatically during the printing process with periodic sampling during a single printing or multiple printings. This way fountain solution flow rate adjustment can be made "on the fly", reducing or eliminating the production of printings having undesired lessened quality.

In examples, the controller 60 may compare the measured drag force to a target drag force value that may correspond to the desired fountain solution thickness. In this instance, fountain solution thickness may not need to be determined from the measured drag force, as drag force values may generally correspond to a range of fountain solution thickness such that the controller 60 may compare the measured drag force to a target drag force value and adjust fountain solution flow based on the comparison. It is understood that the measured drag force and target drag force may be determined as total drag/shear forces of the fountain solution layer 32 or as delta drag/shear forces on the measured surface (e.g., reimageable surface 26, intermediate roller 30 surface) dry versus with the fountain solution layer 32 on the measured surface.

The target drag force may be predefined or determined via multiple approaches and scope is not limited to any particular approach. In examples, the target drag force may be determined off line by applying various amounts of fountain solution on a surface and measuring the drag force and fountain solution thickness to correlate specific drag force to specific fountain solution layer thickness. Target fountain solution thickness (or target drag force) may also be determined via print performance setup procedure. For example, a diagnostic approach where the amount or thickness of fountain solution is intentionally varied while print image quality (IQ) is monitored (e.g., using in-line/offline camera or other scanner system or in-line/offline visual inspection by operator). Based on the fountain solution amount and corresponding print image quality, this approach may be used to determine the target fountain solution thickness/drag force that yields optimal print IQ. The target drag force value may be predefined and stored in a data storage device 84 (FIG. 6).

In other examples, the controller 60 may estimate a thickness of the applied fountain solution fluid layer based on the measured drag force value and modify fountain solution dispense rate based on the estimated thickness of the applied fountain solution fluid layer. For example, the controller 60 may estimate or determine fountain solution thickness via a lookup table or database stored in data storage device 84 (FIG. 6) of the controller, with the lookup table/database providing estimates of fountain solution thickness based on measured drag force. The controller 60 may then compare the estimated thickness of the applied fountain solution fluid layer with a target thickness (e.g., between about 0.01 μm and about 1.0 μm, less than 5 μm, about 30-100 nm), and adjust the fountain solution dispense rate as needed based on the comparison between the estimated thickness of the applied fountain solution fluid layer and the target thickness.

The controller 60 may thus modify or direct modification of the fountain solution dispense rate based on the drag force sensor 58 measurement, or based on the fountain solution layer thickness determined or estimated according to the drag force measurement. The controller 60 may determine the fountain solution thickness by correlating drag force measurements of the fountain solution layer 32 on the fountain solution carrier roller (e.g., imaging member 24, intermediate roller 30) surface to fountain solution thickness. The controller 60 may access a lookup table (LUT) in data storage device 84 (FIG. 6) for correlation between drag force and fountain solution thickness. Further, the controller 60 may access the LUT to determine an amount of modification of the fountain solution flow rate is needed to reach or maintain the desired fountain solution layer thickness.

While measurement of the fountain solution thickness is not required for the print process discussed herein including modifying fountain solution dispense/deposition rate in real time, the inventors found it is highly desirable to measure fountain solution layer drag force that directly correlates to the fountain solution thickness. To this end, the digital image forming device 10 can control fountain solution thickness on the imaging member surface 26 regardless of knowing the actual thickness. For example, upon measuring the fountain solution layer drag force on the fountain solution carrier roller (e.g., imaging member 24, intermediate roller 30) surface with the sensor 58, the controller 60 may then compare the measured drag force with a target drag force corresponding to the desired fountain solution layer thickness and modify the fountain solution dispense or flow rate accordingly, for example with drag force inversely proportional to fountain solution thickness. It is also understood that the drag force measurement and fountain solution dispense rate modification may occur at different times and is not limited to occurrence during a print job by the digital image forming device 10. In other words, drag force measurement and fountain solution dispense rate modification may occur during a print job, between print jobs, or even when no print job is scheduled.

FIG. 6 illustrates a block diagram of the controller 60 for executing instructions to automatically control the digital image forming device 10 and components thereof. The exemplary controller 60 may provide input to or be a component of the digital image forming device for executing the image formation method including controlling fountain solution thickness in a system such as that depicted in FIGS. 1-4, and described in greater detail below.

The exemplary controller 60 may include an operating interface 80 by which a user may communicate with the exemplary control system. The operating interface 80 may be a locally-accessible user interface associated with the digital image forming device 10. The operating interface 80 may be configured as one or more conventional mechanism common to controllers and/or computing devices that may permit a user to input information to the exemplary controller 60. The operating interface 80 may include, for example, a conventional keyboard, a touchscreen with "soft" buttons or with various components for use with a compatible stylus, a microphone by which a user may provide oral commands to the exemplary controller 60 to be "translated" by a voice recognition program, or other like device by which a user may communicate specific operating instructions to the exemplary controller. The operating interface 80 may be a part or a function of a graphical user interface (GUI) mounted on, integral to, or associated with, the digital image forming device 10 with which the exemplary controller 60 is associated.

The exemplary controller 60 may include one or more local processors 82 for individually operating the exemplary controller 60 and for carrying into effect control and operating functions for image formation onto a print substrate 34, including rendering digital images, measuring drag force to determine drag force and/or thickness of fountain solution applied by a fountain solution applicator on a fountain solution carrier roller (e.g., imaging member 24, intermediate roller 30) surface, and/or to determine image forming device real-time image forming modifications for subsequent printings. For example, in real-time during the printing of a print job, based on the measured drag force of the fountain solution layer or film on the fountain solution carrier roller (e.g., imaging member 24, intermediate roller 30), processors 82 may adjust image forming (e.g., fountain solution deposition flow rate) to reach or maintain a preferred fountain solution thickness on the imaging member surface for subsequent (e.g., next) printings of the print job with the digital image forming device 10 with which the exemplary controller may be associated. Processor(s) 82 may include at least one conventional processor or microprocessor that interprets and executes instructions to direct specific functioning of the exemplary controller 60, and control adjustments of the image forming process with the exemplary controller.

The exemplary controller 60 may include one or more data storage devices 84. Such data storage device(s) 84 may be used to store data or operating programs to be used by the exemplary controller 60, and specifically the processor(s) 82. Data storage device(s) 84 may be used to store information regarding, for example, digital image information, printed image response data, fountain solution thickness corresponding to drag force, a target fountain solution thickness and/or corresponding target drag force, and other fountain solution deposition information with which the digital image forming device 10 is associated. Stored fountain solution drag force and thickness data may be devolved into data to generate a recurring, continuous or closed loop feedback fountain solution deposition rate modification in the manner generally described by examples herein.

The data storage device(s) 84 may include a random access memory (RAM) or another type of dynamic storage device that is capable of storing updatable database information, and for separately storing instructions for execution of image correction operations by, for example, processor(s) 82. Data storage device(s) 84 may also include a read-only memory (ROM), which may include a conventional ROM device or another type of static storage device that stores static information and instructions for processor(s) 82. Further, the data storage device(s) 84 may be integral to the exemplary controller 60, or may be provided external to, and in wired or wireless communication with, the exemplary controller 60, including as cloud-based data storage components.

The data storage device(s) 84 may include non-transitory machine-readable storage medium used to store the device queue manager logic persistently. While a non-transitory machine-readable storage medium is may be discussed as a single medium, the term "machine-readable storage medium" should be taken to include a single medium or multiple media (e.g., a centralized or distributed database, and/or associated caches and servers) that store one or more sets of instructions. The term "machine-readable storage medium" shall also be taken to include any medium that is capable of storing or encoding a set of instruction for execution by the controller 60 and that causes the digital image forming device 10 to perform any one or more of the methodologies of the present invention. The term "machine-readable storage medium" shall accordingly be taken to include, but not be limited to, solid-state memories, and optical and magnetic media.

The exemplary controller 60 may include at least one data output/display device 86, which may be configured as one or more conventional mechanisms that output information to a user, including, but not limited to, a display screen on a GUI of the digital image forming device 10 or associated image forming device with which the exemplary controller 60 may be associated. The data output/display device 86 may be used to indicate to a user a status of the digital image forming device 10 with which the exemplary controller 60 may be associated including an operation of one or more individually controlled components at one or more of a plurality of separate image processing stations or subsystems associated with the image forming device.

The exemplary controller 60 may include one or more separate external communication interfaces 88 by which the exemplary controller 60 may communicate with components that may be external to the exemplary control system such as drag force meter 58 that can monitor fountain solution layer 32 drag force and related thickness. At least one of the external communication interfaces 88 may be configured as an input port to support connecting an external CAD/CAM device storing modeling information for execution of the control functions in the image formation and correction operations. Any suitable data connection to provide wired or wireless communication between the exemplary controller 60 and external and/or associated components is contemplated to be encompassed by the depicted external communication interface 88.

The exemplary controller 60 may include an image forming control device 90 that may be used to control an image correction process including fountain solution deposition rate control and modification to render images on imaging member surface 26 having a desired fountain solution thickness. For example, the image forming control device 90 may render digital images on the reimageable surface 26 having a desired fountain solution thickness from fountain solution flow adjusted automatically in real-time based on fountain solution drag force measurements during prior printings of the same print job. The image forming control device 90 may operate as a part or a function of the processor 82 coupled to one or more of the data storage devices 84 and the digital image forming device 10 (e.g., optical patterning subsystem 16, inking apparatus 18, dampening station 12), or may operate as a separate stand-alone component module or circuit in the exemplary controller 60.

All of the various components of the exemplary controller 60, as depicted in FIG. 6, may be connected internally, and to the digital image forming device 10, associated image forming apparatuses downstream the image forming device and/or components thereof, by one or more data/control busses 92. These data/control busses 92 may provide wired or wireless communication between the various components of the image forming device 10 and any associated image forming apparatus, whether all of those components are housed integrally in, or are otherwise external and connected to image forming devices with which the exemplary controller 60 may be associated.

It should be appreciated that, although depicted in FIG. 6 as an integral unit, the various disclosed elements of the exemplary controller 60 may be arranged in any combination of sub-systems as individual components or combinations of components, integral to a single unit, or external to, and in wired or wireless communication with the single unit of the exemplary control system. In other words, no specific configuration as an integral unit or as a support unit is to be implied by the depiction in FIG. 6. Further, although depicted as individual units for ease of understanding of the details provided in this disclosure regarding the exemplary controller 60, it should be understood that the described functions of any of the individually-depicted components, and particularly each of the depicted control devices, may be undertaken, for example, by one or more processors 82 connected to, and in communication with, one or more data storage device(s) 84.

Figure 7:
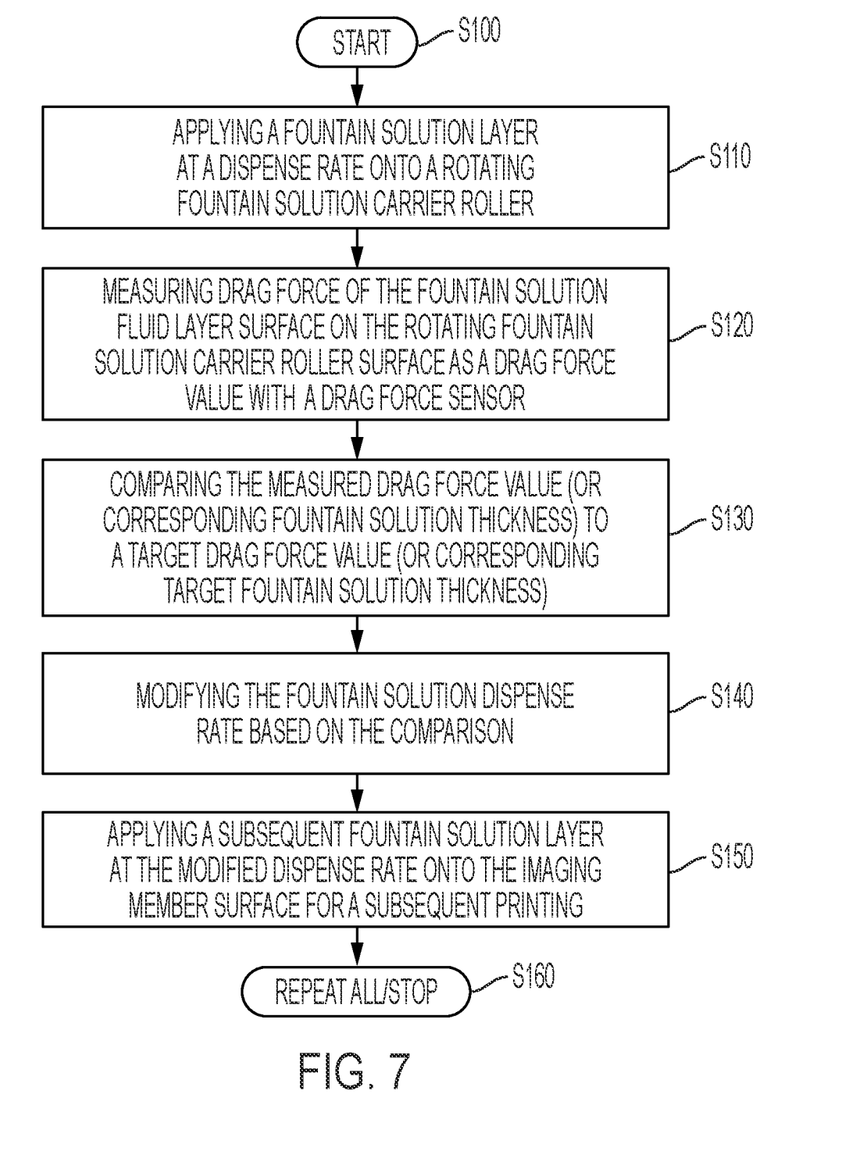
FIG. 7 is a flowchart depicting the operation of an exemplary image forming device.

The disclosed embodiments may include an exemplary method for controlling fountain solution thickness on an imaging member surface of a rotating imaging member in a digital image forming device 10. FIG. 7 illustrates a flowchart of such an exemplary method. As shown in FIG. 7, operation of the method commences at Step S100 and proceeds to Step S110.

At Step S110, a fountain solution applicator 14 applies a fountain solution fluid layer 32 at a dispense rate onto a rotating fountain solution carrier roller, which may be, for example an imaging member 24 or intermediate roller 30 surface. The fountain solution fluid layer 32 is deposited on the fountain solution carrier roller changes drag force on the surface thereof. Operation of the method proceeds to Step S120, where drag force meter 58 measures drag force of the fountain solution fluid on the rotating carrier roller surface as a drag force value. In examples, the drag force meter 58 may measure drag force as its sensor head 94 rest against the rotating carrier roller with strain gauge 98 measuring a difference in drag force caused by the deposited fountain solution on the carrier roller surface rotating against the sensor head.

After the drag force measurement, the controller 60 may estimate the thickness of the applied fountain solution fluid layer 32 that corresponds to the measured drag force value, for example as described in greater detail above. Operation proceeds to Step S130, where the controller 60 compares the measured drag force value (or corresponding fountain solution thickness) to a target drag force value (or corresponding target fountain solution thickness). In examples the target drag force value corresponds to the target fountain solution thickness (e.g., between about 0.01 µm and about 1.0 µm, less than 5 µm, about 30-150 nm) desired for optimal printing as understood by a skilled artisan. If the measured drag force value or corresponding fountain solution thickness is higher than the target drag force value or corresponding target fountain solution thickness, then too much fountain solution is being applied to the imaging member surface, and the laser may not be able to sufficiently boil/evaporate/ablate the fountain solution layer to create a clear latent image on the blanket. If the measured drag force value or corresponding fountain solution thickness is lower than the target drag force value or corresponding target fountain solution thickness, then too little fountain solution is being applied to the imaging member surface, and subsequently applied ink will not be sufficiently rejected in non-imaged regions leading to overly thick ink images with too much background. Information regarding corresponding drag force and fountain solution thickness, as well as target fountain solution drag force/thickness information may be stored in data storage device 84 as depicted in FIG. 6 or as a lookup table for access to the controller 60.

Operation of the method proceeds to Step S140, where the fountain solution dispense rate is modified as needed based on the comparison for subsequent printing using the modified fountain solution dispense rate. The fountain solution dispense rate may be modified by the digital image forming device 10 via instruction from the controller 60. For example, if the measured drag force value is lower than the target drag force or corresponding fountain solution thickness is higher than the corresponding target fountain solution thickness, then the fountain solution dispense rate is lowered accordingly. Further, if the measured drag force value is higher than the target drag force or corresponding fountain solution thickness is lower than the corresponding target fountain solution thickness, then the fountain solution dispense rate is increased accordingly. In examples, the drag force is inversely proportional to fountain solution thickness.

Operation of the method proceeds to Step S150, where the fountain solution applicator 14 applies a subsequent fountain solution fluid layer 32 at the modified dispense rate onto the imaging member surface 26 for a subsequent printing. Operation may cease at Step S160, or may continue by repeating back to Step S120 where drag force meter 58 measures drag force of the fountain solution fluid layer now on the imaging member surface as a drag force value.

The exemplary depicted sequence of executable method steps represents one example of a corresponding sequence of acts for implementing the functions described in the steps. The exemplary depicted steps may be executed in any reasonable order to carry into effect the objectives of the disclosed embodiments. No particular order to the disclosed steps of the method is necessarily implied by the depiction in FIG. 7, and the accompanying description, except where any particular method step is reasonably considered to be a necessary precondition to execution of any other method step. Individual method steps may be carried out in sequence or in parallel in simultaneous or near simultaneous timing. Additionally, not all of the depicted and described method steps need to be included in any particular scheme according to disclosure.

Those skilled in the art will appreciate that other embodiments of the disclosed subject matter may be practiced with many types of image forming elements common to offset inking system in many different configurations. For example, although digital lithographic systems and methods are shown in the discussed embodiments, the examples may apply to analog image forming systems and methods, including analog offset inking systems and methods. It should be understood that these are non-limiting examples of the variations that may be undertaken according to the disclosed schemes. In other words, no particular limiting configuration is to be implied from the above description and the accompanying drawings.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art.

What is claimed is:

1. A method of controlling fountain solution thickness on an imaging member surface of a rotating imaging member in a digital image forming device, comprising:
    (a) transferring a layer of fountain solution from a fountain solution applicator having a fountain solution dispense rate onto a fountain solution carrier roller;
    (b) measuring a drag force of the fountain solution layer between a sensor head and the fountain solution carrier roller, with the fountain solution layer being a lubricant between the sensor head and the fountain solution carrier roller;
    (c) modifying the fountain solution dispense rate based on the measured drag force; and
    (d) applying a subsequent fountain solution layer at the modified fountain solution dispense rate onto the imaging member surface for an image forming operation thereon.

2. The method of claim 1, further comprising, after Step (b), comparing the measured drag force to a target drag force, and Step (c) includes modifying the fountain solution dispense rate based on the comparison between the measured drag force and the target drag force.

3. The method of claim 1, further comprising, after Step (b), estimating a thickness of the applied fountain solution fluid layer based on the measured drag force, and Step (c) includes modifying the fountain solution dispense rate based on the estimated thickness of the applied fountain solution fluid layer.

4. The method of claim 3, further comprising comparing the estimated thickness of the applied fountain solution fluid layer with a target thickness, and Step (c) further includes modifying the fountain solution dispense rate based on the comparison between the estimated thickness of the applied fountain solution fluid layer and the target thickness.

5. The method of claim 1, further comprising, before Step (b) moving the sensor head into contact with the fountain solution carrier roller, and after Step (b) moving the sensor head away from contact with the fountain solution carrier roller.

6. The method of claim 1, wherein the fountain solution carrier roller is the imaging member, and Step (a) includes depositing the layer of fountain solution from the fountain solution applicator onto the imaging member at the fountain solution dispense rate.

7. The method of claim 1, wherein the fountain solution carrier roller is a vapor deposition roller between the fountain solution applicator and an imaging member, Step (a) includes depositing the layer of fountain solution from the fountain solution applicator onto the vapor deposition roller at the fountain solution dispense rate, and Step (d) includes applying the subsequent fountain solution layer at the modified fountain solution dispense rate onto the vapor deposition roller, and then transferring the subsequent fountain solution layer from the vapor deposition roller to the imaging member surface for the image forming operation thereon.

8. A method of controlling fountain solution thickness on an imaging member surface of a rotating imaging member in a digital image forming device, the digital image forming device printing a current image onto a print substrate, the printing including applying a fountain solution layer at a dispense rate onto the imaging member surface, the fountain solution fluid layer having a surface above the imaging member surface, vaporizing in an image wise fashion a portion of the fountain solution layer to form a latent image, applying ink onto the latent image over the imaging member surface, and transferring the applied ink from the imaging member surface to the print substrate, the method of controlling fountain solution thickness comprising:
    (a) transferring the layer of fountain solution from a fountain solution applicator having a fountain solution dispense rate onto a fountain solution carrier roller;
    (b) measuring a drag force of the fountain solution layer between a sensor head and the fountain solution carrier roller, with the fountain solution layer being a lubricant between the sensor head and the fountain solution carrier roller;
    (c) modifying the fountain solution dispense rate based on the measured drag force; and
    (d) printing a subsequent image by the digital image forming device using the modified fountain solution dispense rate.

9. The method of claim 8, further comprising, after Step (b), comparing the measured drag force to a target drag force, and Step (c) includes modifying the fountain solution dispense rate based on the comparison between the measured drag force and the target drag force.

10. The method of claim 8, further comprising, after Step (b), estimating a thickness of the applied fountain solution fluid layer based on the measured drag force, and Step (c) includes modifying the fountain solution dispense rate based on the estimated thickness of the applied fountain solution fluid layer.

11. The method of claim 10, further comprising comparing the estimated thickness of the applied fountain solution fluid layer with a target thickness, and Step (c) further includes modifying the fountain solution dispense rate based on the comparison between the estimated thickness of the applied fountain solution fluid layer and the target thickness.

12. The method of claim 8, further comprising, before Step (b) moving the sensor head into contact with the fountain solution carrier roller, and after Step (b) moving the sensor head away from contact with the fountain solution carrier roller.

13. The method of claim 8, wherein the fountain solution carrier roller is the imaging member, and Step (a) includes depositing the layer of fountain solution from the fountain solution applicator onto the imaging member at the fountain solution dispense rate.

14. The method of claim 8, wherein the fountain solution carrier roller is a vapor deposition roller between the fountain solution applicator and an imaging member, Step (a) includes depositing the layer of fountain solution from the fountain solution applicator onto the vapor deposition roller at the fountain solution dispense rate, and Step (d) includes applying a subsequent fountain solution layer at the modified fountain solution dispense rate onto the vapor deposition roller, and transferring the subsequent fountain solution layer from the vapor deposition roller to the imaging member surface for the printing.

15. A digital image forming device controlling fountain solution thickness on an imaging member surface of a rotating imaging member, comprising:
   a fountain solution carrier roller;
   a fountain solution applicator configured to apply a fountain solution fluid layer at a dispense rate, the fountain solution fluid layer being transferred onto the fountain solution carrier roller;
   a sensor including a sensor head adjacent the fountain solution carrier roller and in contact with the fountain solution fluid layer, the sensor configured to measure a drag force of the fountain solution layer between the sensor head and the fountain solution carrier roller, the fountain solution layer being a lubricant between the sensor head and the fountain solution carrier roller; and
   a controller in communication with the sensor and the fountain solution applicator to modify the fountain solution dispense rate based on the measured drag force,
   the fountain solution applicator configured to apply a subsequent fountain solution layer at the modified fountain solution dispense rate onto the imaging member surface for an image forming operation thereon.

16. The digital image forming device of claim 15, wherein the fountain solution carrier roller is the imaging member, and the fountain solution applicator is configured to transfer the fountain solution fluid layer by depositing the fountain solution onto the imaging member at the fountain solution dispense rate.

17. The digital image forming device of claim 15, wherein the fountain solution carrier roller is a vapor deposition roller between the fountain solution applicator and an imaging member, and the fountain solution applicator is configured to transfer the fountain solution fluid layer by depositing the fountain solution onto the vapor deposition roller at the fountain solution dispense rate.

18. The digital image forming device of claim 15, wherein the sensor head is spherical.

19. The digital image forming device of claim 15, wherein the fountain solution carrier roller is the imaging member, and Step (a) includes depositing the layer of fountain solution from the fountain solution applicator onto the imaging member at the fountain solution dispense rate.

20. The digital image forming device of claim 15, wherein the fountain solution carrier roller is a vapor deposition roller between the fountain solution applicator and an imaging member, Step (a) includes depositing the layer of fountain solution from the fountain solution applicator onto the vapor deposition roller at the fountain solution dispense rate, and Step (d) includes applying the subsequent fountain solution layer at the modified fountain solution dispense rate onto the vapor deposition roller, and then transferring the subsequent fountain solution layer from the vapor deposition roller to the imaging member surface for the image forming operation thereon.

* * * * *